United States Patent [19]

Berger et al.

[11] 4,178,290

[45] Dec. 11, 1979

[54] DITHIINOACETIC ACID AND ITS PREPARATION

[75] Inventors: Christian Berger, Le Plessis Robinson; Dominique Deprez, Longjumeau; Daniel Farge, Thiais; Claude Moutonnier, Le Plessis Robinson; Gerard Wolff, Vitry, all of France

[73] Assignee: Rhone-Poulenc Industries, Paris, France

[21] Appl. No.: 913,088

[22] Filed: Jun. 6, 1978

[30] Foreign Application Priority Data

Jun. 9, 1977 [FR] France .................. 77 17663
Mar. 29, 1978 [FR] France .................. 78 09042
Mar. 30, 1978 [FR] France .................. 78 09224

[51] Int. Cl.² ........................... C07D 339/08
[52] U.S. Cl. ........................ 549/22; 544/22; 544/16; 544/19
[58] Field of Search ................... 260/327 M

[56] References Cited

FOREIGN PATENT DOCUMENTS 2543000  4/1976  Fed. Rep. of Germany ............. 544/28
2543001  4/1976  Fed. Rep. of Germany ............. 544/28

OTHER PUBLICATIONS

Berger et al., Chemical Abstracts, vol. 85, abst. 3351a (1976), (abst. of German Offen. No. 2,543,000).
Berger et al., Chemical Abstracts, vol. 85, abst. 46698a (1976), (abst. of German Offen. No. 2,543,001).

*Primary Examiner*—John M. Ford
*Assistant Examiner*—Robert T. Bond
*Attorney, Agent, or Firm*—Stevens, Davis, Miller & Mosher

[57] ABSTRACT

α-Amino(1,3-dithiin-5-yl)-acetic acid in the D-, L-, or D,L-form and in which the amino radical is free or protected by tert.-butoxycarbonyl or 2,2,2-trichloroethoxycarbonyl is a useful intermediate in the preparation of cephalosporins having valuable antibacterial activity.

5 Claims, No Drawings

DITHIINOACETIC ACID AND ITS PREPARATION

The present invention provides the new compound 1,3-dithiino-acetic acid of the formula:

  (I)

in which the amine function is free or protected by a tert.-butoxycarbonyl or 2,2,2-trichloroethoxycarbonyl radical, in its D, L and D,L forms.

According to a feature of the invention, the acid of the formula (I) in which the amine function is free can be obtained by deformylating α-formylamino-(1,3-dithiin-5-yl)-acetic acid.

The reaction is generally carried out in an aqueous acid medium at a temperature of between 0° and 100° C. A mineral acid, such as a solution of hydrochloric acid in water, is preferably used, at a temperature of about 100° C.

α-Formylamino-(1,3-dithiin-5-yl)-acetic acid can be obtained by saponifying the corresponding ester of the general formula:

  (II)

in which $R_6$ represents an alkyl radical containing 1 to 4 carbon atoms, the reaction being carried out under conditions which make it possible to saponify the ester to give the corresponding acid without affecting the rest of the molecule. The ester to be saponified is generally treated with an alkali metal hydroxide in an aqueous-alcoholic medium at a temperature of between 0° and 50° C. Preferably, the methyl or ethyl ester is used and the saponification is carried out in an aqueous methanolic or aqueous-ethanolic medium at a temperature of about 5° C.

The ester of the general formula (II) can be obtained by the action of an isocyanoacetate of the general formula:

$$CN-CH_2-COOR_6 \quad (III)$$

in which $R_6$ is as previously defined, on 1,3-dithiacyclohexan-5-one. The reaction is generally carried out in an anhydrous organic solvent such as tetrahydrofuran, in the presence of an alkaline condensation agent such as potassium tert.-butylate and at a temperature of between −70° and 0° C.

The isocyanoacetate of the general formula (III) can be prepared in accordance with the method described by U. SCHÖLLKOPF et al., Chem. Ber., 108, 1580 (1975).

1,3-Dithiacyclohexan-5-one can be prepared in accordance with the method described by E. G. HOWARD and R. V. LINDSEY, J. Amer. Chem. Soc., 82, 158 (1960).

According to a further feature of the invention, the acid of the formula (I) can be obtained by saponifying the ester of the formula:

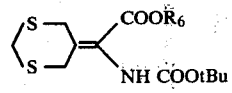  (IV)

in which $R_6$ is as defined above, and then optionally removing the protective tert.-butoxycarbonyl group of the amine function.

The saponification is advantageously carried out in an aqueous-alcoholic medium by treatment with an alkali metal hydroxide at a temperature of between 0° and 50° C. Preferably, sodium hydroxide is used and the methyl or ethyl ester is treated in an aqueous-methanolic or aqueous-ethanolic medium at a temperature of about 20° C.

When it is desired to obtain a product of the formula (I) in which the amine function is free, the protective group is generally removed in the presence of trifluoroacetic acid at a temperature of between 0° and 30° C.

The ester of the general formula (IV) can be obtained by the action of potassium tert.-butylate on a product of the general formula:

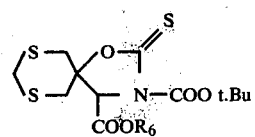  (V)

in which $R_6$ is defined as previously. The reaction is generally carried out in an organic solvent such as tetrahydrofuran at a temperature of between −78° and 0° C.

The product of the general formula (V) can be obtained by the action of an alkyl (e.g. ethyl) isothiocyanatoacetate on 1,3-dithiacyclohexan-5-one in the presence of potassium tert.-butylate, followed by the action of di-tert.butyl dicarbonate. The reaction is generally carried out in a solvent such as tetrahydrofuran at a temperature of between −78° and 0° C.

The optically active forms of the acid of the formula (I) can be obtained by applying physico-chemical methods or by an enzymatic route. When it is desired to obtain the D or L forms of the acid of the formula (I), it can be advantageous to separate the optically active forms before removing the protective group of the amine function. For example, the racemic form can be treated with quinine in a solvent such as methyl ethyl ketone.

The salts of the D and L forms are purified by crystallisation; the free D and L acids are isolated from these salts and the protective group of the amine function is then removed in order to obtain the D and L forms of the aminoacid of the formula (I).

The new acid of the formula (I) constitutes a useful intermediate for the preparation of new therapeutically active cephalosporin derivatives of the general formula:

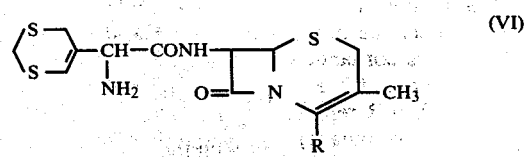  (VI)

in which R represents a carboxyl radical or a radical of the general formula:

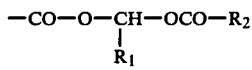

(VII)

in which $R_1$ represents a hydrogen atom or an alkyl radical containing 1 to 4 carbon atoms and $R_2$ represents a straight or branched-chain alkyl radical containing 1 to 4 carbon atoms, or a cyclohexyl radical, the radical $$-\underset{\underset{R_1}{|}}{CH}-OCO-R_2 \quad \text{(VIII)}$$

being a radical which is easily removable by an enzymatic route, it being understood that the products of the general formula (VI) are derived from the D, L and D,L forms of the aminoacid of the formula (I).

The new products of the general formula (VI) can be obtained by the action of the acid of the formula (I), which is in the racemic or optically active form and in which the amine function has been protected beforehand, or a reactive derivative of this acid, on a cephalosporin of the general formula:

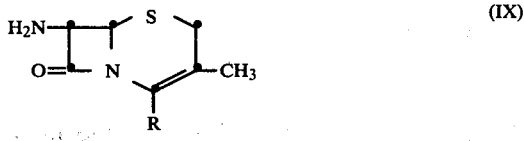

(IX)

in which R is defined as previously.

(a) When the acid of the formula (I) is used, the amino group is protected by any method which is in itself known for blocking an amine function without affecting the rest of the molecule. It is necessary to use an easily removable group such as the tert.-butoxycarbonyl or 2,2,2-trichloroethoxycarbonyl group. It is particularly advantageous to use the tert.-butoxycarbonyl group which can be introduced by the action of di-tert.-butyl dicarbonate, tert.-butyl azidoformate, tert.-butyl chloroformate or the mixed tert.-butyl/p-nitrophenyl carbonate.

It is also possible to protect the amino radical in the form of an enamine of the general formula:

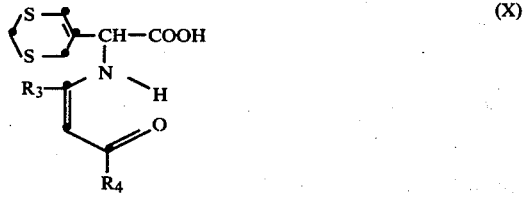

(X)

in which the symbol $R_3$ represents an alkyl radical containing 1 to 4 carbon atoms and the symbol $R_4$ represents an alkyl radical containing 1 to 4 carbon atoms, an alkoxy radical in which the alkyl part contains 1 to 4 carbon atoms, or a phenyl radical.

The enamine of the general formula (X) can be prepared in accordance with the method described by E. DANE et al., Chem. Ber., 98, 789 (1965).

(α) When R represents a carboxyl radical, the product of the formula (I), in which the acid function is free and the amine function has been protected beforehand, is generally condensed with 7-amino-3-deacetoxycephalosporanic acid in which the acid function has been protected beforehand by an easily removable group such as the benzhydryl, tert.-butyl or 2,2,2-trichloroethyl radical.

The condensation is generally carried out in an organic solvent such as dimethylformamide, acetonitrile, tetrahydrofurane or chloroform, in the presence of a condensation agent such as a carbodiimide (e.g. dicyclohexylcarbodiimide) or N,N'-carbonyldiimidazole and at a temperature of between 0° and 40° C., and the protective groups of the amine and acid functions are then removed.

This removal can be carried out in a single stage or in two stages, depending on the nature of the protective groups.

When the protective group of the amine function is a tert.-butoxycarbonyl radical, then, depending on the nature of the protective group of the acid function, the removal is carried out:

in a single phase by treatment in an acid medium, when the acid function is protected by a tert.-butyl or benzhydryl group. Preferably, trifluoroacetic acid is used, the reaction being carried out at a temperature of between 0° and 20° C. and, in the case of the benzhydryl radical, in the presence of anisole. Under these conditions, the product of the general formula (VI) is obtained in the form of the trifluoroacetate from which the amine function can be liberated by any method which is in itself known for obtaining an amine from one of its salts without affecting the rest of the molecule, in particular by bringing the salt into contact with an ion exchange resin (e.g. a polystyreneamine resin such as Amberlite IR-45).

by treatment with zinc in acetic acid and then replacement of the tert.-butoxycarbonyl radical by treatment in an acid medium, when the acid function is protected by the 2,2,2-trichloroethyl radical. The treatment in an acid medium is carried out using trifluoroacetic acid; under these conditions, the product of the general formula (VI) is obtained in the form of the trifluoroacetate and the free amine can be liberated from its salt under the conditions described previously.

When the protective group of the amine function is a 2,2,2-trichloroethoxycarbonyl radical, then, depending on the nature of the protective group of the acid function, the removal is carried out:

by treatment with zinc in acetic acid and then treatment in an acid medium, preferably by the action of trifluoroacetic acid, when the protective group of the acid function is a tert.-butyl or benzhydryl radical, or by treatment with zinc in acetic acid, when the protective group of the acid function is a 2,2,2-trichloroethyl radical.

When the amine function is protected in the form of an enamine, then, depending on the nature of the protective group of the acid function, the removal is carried out:

by hydrolysis in a dilute acid medium, e.g. in the presence of hydrochloric acid, and then treatment with trifluoroacetic acid, when the protective group of the acid function is a tert.-butyl or benzhydryl radical, or by hydrolysis in an acid medium, e.g. in the presence of hydrochloric acid, and then treatment with zinc in acetic acid, when the protective group of the acid function is a 2,2,2-trichloroethyl radical.

(β) When R represents a radical of the general formula (VII), as defined previously, the acid of the formula (I) is generally condensed with the derivative of the general formula (IX) in an organic solvent such as dimethylformamide or chloroform, in the presence of a condensation agent such as a carbodiimide (e.g. dicyclohexylcarbodiimide) or N,N'-carbonyldiimidazole and at a temperature of between 0° and 40° C., and the protective group of the amine function is then removed under the conditions described above.

(b) When a derivative of the acid of the formula (I) is used, it is advantageous to employ the anhydride, a mixed anhydride or a reactive ester of the general formula:

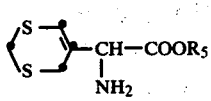  (XI)

in which $R_5$ represents a succinimido, benzotriazol-1-yl or 2,4-dinitrophenyl radical and in which the amine function has been protected beforehand; it is also advantageous to employ the acid chloride by reacting the hydrochloride of the chloride of the acid of the formula (I) with the cephalosporin of the general formula (IX). It is also possible to use the Leuchs' anhydride.

When employing the anhydride, a mixed anhydride, Leuchs' anhydride or the acid chloride (which can all be prepared in situ), the condensation is carried out in an organic solvent such as tetrahydrofurane, chloroform or methylene chloride, in the presence of an acid acceptor such as an organic nitrogen-containing base like pyridine or triethylamine, or in an aqueous-organic medium, in the presence of an alkaline condensation agent such as sodium bicarbonate, the reaction being carried out at a temperature of between $-40°$ and $+40°$ C., and the protective group of the amine function is then optionally replaced by a hydrogen atom. In the case where R represents a carboxyl radical, it is not necessary to protect the acid function.

When employing a reactive ester of the general formula (XI), the reaction is generally carried out in the presence of triethylamine in an organic solvent such as dimethylformamide, at a temperature of between 0° and 40° C., and the protective group of the amine function is then replaced by a hydrogen atom. In the case where R represents a carboxyl radical, it is not necessary to protect the acid function.

The product of the general formula (IX) in which R represents the carboxyl radical is 7-amino-3-deacetoxycephalosporanic acid (or 7-ADCA); it can be obtained either from a penicillin in accordance with the process which forms the subject of Belgian Patent 747,382, or by deacetoxylating 7-aminocephalosporanic acid (or 7-ACA) in accordance with the process which forms the subject of Belgian Pat. No. 779,034.

The product of the general formula (IX) in which R represents a radical of the general formula (VII), in which $R_1$ and $R_2$ are defined as previously, can be prepared from 7-amino-3-deacetoxycephalosporanic acid by any method which is in itself known for preparing an ester from an acid without affecting the rest of the molecule.

In general, an alkali metal salt or a tertiary amine salt of 7-amino-3-deacetoxycephalosporanic acid is reacted with a halide of the general formula:

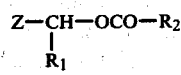  (XII)

in which $R_1$ and $R_2$ are defined as previously and Z represents a halogen atom, in an inert solvent such as dimethylformamide and at a temperature of between 0° and 30° C.

The products of the general formula (XII) can be prepared in accordance with the method described in German Patent Application No. 2,350,230.

The products of the general formula (VI) can optionally be purified by physical methods such as crystallisation or chromatography.

The products of the general formula (VI) can be converted into addition salts with acids. In accordance with the processes indicated above, the products are generally obtained in the form of the trifluoroacetate. The products of the general formula (VI) obtained in the form of this salt can be liberated and converted into other salts in accordance with the usual methods.

The products of the general formula (VI) in which R represents the carboxyl radical can also be converted into metal salts or into addition salts with organic nitrogen-containing bases in accordance with the methods which are in themselves known. These salts can be obtained by the action of an alkali metal or alkaline earth metal base or an amine on a product of the general formula (VI) is an appropriate solvent such as an alcohol, an ether or water, or by an exchange reaction with a salt of an organic acid. The salt which is formed precipitates, after concentration, if necessary, of its solution, and it is separated off by filtration or decantation.

The cephalosporin derivatives of the general formula (VI) exhibit particularly valuable anti-bacterial properties. They show a remarkable in vitro and in vivo activity against Gram-positive and Gram-negative germs.

In vitro, the products of the general formula (VI) have shown themselves to be active at a concentration of between 2 and 15 µg/cc against staphylococcus strains which are sensitive to penicillin G (*Staphylococcus aureus* Smith), at a concentration of between 10 and 150 µg/cc against staphylococcus strains which are resistant to penicillin G (*Staphylococcus aureus* MB 9), at a concentration of between 0.125 and 1.5 µg/cc against *Streptococcus pyogenes* Dig 7, at a concentration of between 2 and 30 µg/cc against *Escherichia coli*, Monod strain, at a concentration of between 4 and 30 µg/cc against *Klebsiella pneumoniae*, at a concentration of between 1 and 8 µg/cc against *Salmonella typhi*, at a concentration of between 1 and 8 µg/cc against *Shigella flexneri* and at a concentration of between 5 and 20 µg/cc against *Proteus mirabilis*.

In vivo, the products of the general formula (VI) have shown themselves to be active against experimental infections in mice with *Staphylococcus aureus* Smith (sensitive to penicillin G) at a dose of between 0.05 and 0.6 mg/kg, administered orally or subcutaneously, and with *Escherichia coli* at a dose of between 1 and 6 mg/kg, administered orally or subcutaneously.

When administered subcutaneously, these products are shown to be non-toxic at a dose of 2.5 g/kg in mice.

The following examples, show how the invention can be put into practice.

EXAMPLE 1

A suspension of D,L-α-formylamino-(1,3-dithiin-5-yl)-acetic acid (63 g) in 4 N hydrochloric acid (320 cc) is heated at 90° C. until the solid has completely dissolved. The solution is cooled to 20° C. and treated with decolorising charcoal. The solution is filtered and then brought to pH=4.5 by adding 4 N sodium hydroxide. The precipitate which has appeared is filtered off. D,L-α-Amino-(1,3-dithiin-5-yl)-acetic acid (41 g) is thus obtained in the form of a white solid which melts at about 270° C. with decomposition.

D,L-α-Formylamino-(1,3-dithiin-5-yl)-acetic acid can be prepared in the following manner:

A suspension of an equilibrium mixture (72 g) of ethyl α-formylamino-(4,5-dihydro-1,3-dithiin-5-ylidene)-acetate and ethyl D,L-α-formylamino-(1,3-dithiin-5-yl)-acetate in ethanol (720 cc) and water (200 cc) is cooled to 5° C. 4 N sodium hydroxide (80 cc) is added. The reaction mixture is stirred for 90 minutes at 5° C. It is concentrated to a volume of 100 cc under reduced pressure (20 mm Hg). The solution obtained is cooled in an icebath and acidified to pH=2.0 by adding 4 N hydrochloric acid. The precipitate which has appeared is filtered off. Crude D,L-α-formylamino-(1,3-dithiin-5-yl)-acetic acid (67 g) is thus obtained in the form of a white solid.

The mixture of ethyl α-formylamino-(4,5-dihydro-1,3-dithiin-5-ylidene)-acetate and ethyl D,L-α-formylamino(1,3-dithiin-5-yl)-acetate can be prepared in the following manner:

A solution of potassium tert.-butylate (27.2 g) in tetrahydrofurane (200 cc) is cooled to 0° C. A solution of ethyl isocyanoacetate (25 g) in tetrahydrofurane (150 cc) is added dropwise. The mixture is stirred for a further one hour at 0° C. and a solution of 1,3-dithiacyclohexan-5-one (29.6 g) in tetrahydrofurane (375 cc) is then added. The reaction mixture is stirred for a further 90 minutes at 0° C. Acetic acid (50 cc) is added and the precipitate is filtered off. The solvents are evaporated off under reduced pressure (20 mm Hg) at 30° C. The residue is taken up with methylene chloride (2,500 cc). Extraction is carried out with a mixture of water (500 cc) and a saturated aqueous solution of sodium bicarbonate (300 cc). The organic phase is again washed with water (500 cc) and dried over sodium sulphate. The solution is treated with decolorising charcoal, filtered and then concentrated to dryness under reduced pressure (20 mm Hg) at 30° C. The residue is vigorously stirred with ethyl ether (400 cc). The precipitate obtained is filtered off. Ethyl α-formylamino-(4,5-dihydro-1,3-dithiin-5-ylidene)-acetate (18.5 g) is thus obtained. The filtrate is concentrated to dryness under reduced pressure (20 mm Hg) at 20° C. The residue is purified by chromatography on a column (diameter 3.7 cm; height 47 cm) containing silica (250 g). Elution is carried out with a mixture (two liters) of methylene chloride and ethyl acetate (85/15 by volume). A mixture (4.4 g) of ethyl α-formylamino-(4,5-dihydro-1,3-dithiin-5-ylidene)-acetate and ethyl α-formylamino-(1,3-dithiin-5-yl)-acetate is thus obtained.

Ethyl isocyanoacetate can be prepared according to U. SCHÖLLKOPF, D. HOPPE and R. JENTSCH, Chem. Ber., 108, 1,580 (1975).

1,3-Dithiacyclohexan-5-one can be prepared according to E. G. HOWARD and R. V. LINDSEY, J. Amer. Chem. Soc., 82, 158 (1960).

EXAMPLE 2

A suspension of ethyl α-tert.-butoxycarbonylamino-(4,5-dihydro-1,3-dithiin-5-ylidene)-acetate (0.96 g) in ethanol (7 cc) and N sodium hydroxide (3.3 cc) is stirred for 90 minutes at 20° C. It is concentrated to a volume of 5 cc under reduced pressure (20 mm Hg) at 30° C. The solution obtained is acidified to pH=2.0 by adding N hydrochloric acid in the presence of ethyl ether (25 cc). The organic phase is decanted and dried over sodium sulphate. The solution is filtered and concentrated to dryness under reduced pressure (20 mm Hg) at 30° C. D,L-α-Tert.-butoxycarbonylamino-(1,3-dithiin-5-yl)-acetic acid (0.85 g) is thus obtained and has the following characteristics:

Elementary analysis: % Calculated: C 45.34; H 5.88; N 4.80; O 21.97; S 22.01. % Found: C 44.8; H 5.7; N 4.7; S 21.5.

The D- and L-α-tert.-butoxycarbonylamino-(1,3-dithiin-5-yl)-acetic and D- and L-α-amino-(1,3-dithiin-5-yl)-acetic acids can be prepared from this product in the following manner:

(a) A solution of D,L-α-tert.-butoxycarbonylamino-(1,3-dithiin-5-yl)-acetic acid (212 g) and quinine (236 g) in methyl ethyl ketone (4,300 cc) is heated under reflux. It is allowed to cool and left for 3 hours, whilst stirring, and white crystals (169 g) are filtered off and discarded. The filtrate is stirred for 16 hours at ambient temperature. White crystals (150 g) can be isolated by filtration.

A suspension in methyl ethyl ketone (3,750 cc) of the crystals (375 g) thus obtained is heated at 80° C. until the solid has completely dissolved. The solution is allowed to cool and the crystals obtained are then filtered off. The quinine salt of D-α-tert.-butoxycarbonylamino(1,3dithiin-5-yl)-acetic acid (187 g) is thus obtained in the form of white crystals.

The quinine salt of D-α-tert.-butoxycarbonylamino(1,3-dithiin-5-yl)-acetic acid (98.5 g) is added to a stirred mixture of water (2 liters) and ethyl ether (2 liters), keeping the pH at 11 by adding 4 N sodium hydroxide. After dissolution, the aqueous phase is decanted and acidified to pH=1 by adding 4 N hydrochloric acid in the presence of ethyl ether (one liter). The organic phase is decanted and a further extraction is carried out with ethyl ether (one liter). The organic extracts are combined and dried over magnesium sulphate. They are concentrated to dryness under reduced pressure (20 mm Hg) at 30° C. D-α-Tert.-butoxycarbonylamino-(1,3-dithiin-5-yl)-acetic acid (41.7 g) is thus obtained in the form of a yellow oil. The acid (5 g) thus obtained is dissolved in a mixture of isopropyl ether (10 cc) and cyclohexane (25 cc) under reflux. After cooling, the crystals are filtered off. D-α-Tert.-butoxycarbonylamino-(1,3-dithiin-5-yl)-acetic acid (4 g) is thus obtained in the form of white crystals which melt at 110° C. (Kofler instantaneous m.p.). $[\alpha]_D^{20} = -121 \pm 2°$ (c=1, dimethylformamide).

(b) The crystals (200 g) obtained under the conditions described for obtaining the white crystals (169 g) which were previously discarded are dissolved in methyl ethyl ketone (4,000 cc) at 80° C. The solution is allowed to cool and the crystals are then filtered off after 16 hours. These crystals are redissolved in methyl ethyl ketone (3,250 cc) at 80° C. The solution is allowed to cool for 16 hours and the crystals of the quinine salt of L-α-tert.-butoxycarbonylamino-(1,3-dithiin-5-yl)-acetic acid are then filtered off. These crystals are added to a mixture of distilled water (1,500 cc) and ethyl ether (1,500 cc).

The pH is kept at 11 by adding 4 N sodium hydroxide. After dissolution, the aqueous phase is decanted and acidified to pH=1 by adding 4 N hydrochloric acid in the presence of ethyl ether (1,000 cc). The organic phase is decanted and the aqueous phase is extracted with ether (500 cc). The organic extracts are combined and dried over magnesium sulphate. They are concentrated to dryness under reduced pressure (20 mm Hg). L-α-Tert.-butoxycarbonylamino-(1,3-dithiin-5-yl)-acetic acid (50.4 g) is thus obtained in the form of a yellow oil.

$[\alpha]_D^{20} = +121 \pm 20°$ (c=1, dimethylformamide).

(c) A solution of D-α-tert.-butoxycarbonylamino-(1,3-dithiin-5-yl)-acetic acid (3.4 g) in trifluoroacetic acid (34 cc) is stirred for 20 minutes at about 20° C. It is concentrated to dryness under reduced pressure (0.01 mm Hg) at 30° C. and the residue is dissolved in acetone (25 cc) and water (10 cc). Triethylamine is added until a pH of 4.5 is obtained. The white precipitate is filtered off, washed with acetone (10 cc) and dried in vacuo (0.01 mm Hg) at 20° C. The solid thus obtained (1.7 g) is dissolved in N hydrochloric acid (25 cc). The solution is filtered and brought to pH=4.5 by adding 4 N sodium hydroxide. The white crystals are filtered off and dried under reduced pressure (1 mm Hg) at 20° C. D-α-Amino-(1,3-dithiin-5-yl)-acetic acid (1 g) is thus obtained in the form of white crystals.

$[\alpha]_D^{20} = -146.6 \pm 2°$ (c=1, N hydrochloric acid).

Elementary analysis: % Calculated: C 37.67; H 4.74; N 7.33; O 16.73; S 33.53. % Found: C 38.0; H 4.8; N 7.3; O 16.2; S 33.2.

(d) By following the previous procedure of (c), L-α-amino-(1,3-dithiin-5-yl)-acetic acid (27.5 g) is obtained starting from a solution of L-α-tert.-butoxycarbonylamino(1,3-dithiin-5-yl)-acetic acid (50.4 g) in trifluoroacetic acid (250 cc). The L-α-amino-(1,3-dithiin-5-yl)-acetic acid (7 g) thus obtained is dissolved in N hydrochloric acid (150 cc). The filtered solution is brought to pH=4.5 by adding 4 N sodium hydroxide. The crystals obtained are filtered off and dried under reduced pressure (1 mm Hg) at 20° C. L-α-Amino-(1,3-dithiin-5-yl)-acetic acid (5 g) is thus obtained in the form of white crystals.

$[\alpha]_D^{20} = +145 \pm 20°$ (c=1, N hydrochloric acid).

Elementary analysis: % Calculated: C 37.67; H 4.74; N 7.33; O 16.73; S 33.53. % Found: C 37.75; H 4.75; N 7.10; O 16.68; S 33.32.

Ethyl α-tert.-butoxycarbonylamino-(4,5-dihydro-1,3-dithiin-5-ylidene)-acetate can be prepared in the following manner:

A solution of potassium tert.-butylate (5.35 g) in tetrahydrofurane (40 cc) is cooled to −70° C. A solution of 3-tert.-butoxycarbonyl-4-ethoxycarbonyl-2-thioxo-1-oxa-7,9-dithia-3-azaspiro[4.5]decane (9 g) in tetrahydrofurane (40 cc) is added dropwise. The mixture is stirred for a further 3 hours, acetic acid (2.9 g) is then added and the reaction mixture is allowed to warm up to 20° C. The tetrahydrofurane is evaporated off under reduced pressure (20 mm Hg) at 30° C. The residue is dissolved in ethyl acetate (25 cc). The solution is washed with water (25 cc) and then dried over sodium sulphate. The solution is filtered and the filtrate is concentrated to dryness under reduced pressure (20 mm Hg). A solid residue is obtained and treated with petroleum ether (100 cc). The precipitate is filtered off and dried under reduced pressure. Ethyl α-tert.-butoxycarbonylamino-(4,5-dihydro-1,3-dithiin-5-ylidene)-acetate (5.3 g) is thus obtained in the form of a beige solid which melts at 154° C. (Kofler instantaneous m.p.).

3-Tert.-butoxycarbonyl-4-ethoxycarbonyl-2-thioxo-1-oxa-7,9-dithia-3-azaspiro[4.5]decane can be prepared in the following manner:

A solution of potassium tert.-butylate (4.6 g) in tetrahydrofurane (40 cc) is cooled to −70° C. A solution of ethyl isothiocyanatoacetate (5.8 g) and 1,3-dithiacyclohexan-5-one (5.4 g) in tetrahydrofurane (80 cc) is added dropwise. After 40 minutes, the solution is heated to about 0° C. and a solution of di-tert.-butyl dicarbonate (8.75 g) in tetrahydrofurane (10 cc) is added. The mixture is stirred for a further 12 hours at about 20° C. and then concentrated to dryness under reduced pressure (20 mm Hg) at 30° C. The residue is dissolved in methylene chloride (150 cc), acetic acid (3 cc) is added and the insoluble material is filtered off. The filtrate is concentrated to dryness under reduced pressure (20 mm Hg) at 30° C. The residue is crystallised from ethyl ether (100 cc) and then filtered off and dried under reduced pressure (1 mm Hg) at 20° C. 3-Tert.-butoxycarbonyl-4-ethoxycarbonyl-2-thioxo-1-oxa-7,9-dithia-3-azaspiro[4.5]decane (9.8 g) is thus obtained in the form of white crystals which melt at 125° C. (Kofler instantaneous m.p.).

Ethyl isothiocyanatoacetate can be prepared according to D. HOPPE and R. FOLLMANN, Chem. Ber., 109, 3,047 (1976).

EXAMPLE 3

Sodium carbonate (10.6 g) and then a solution of di-tert.-butyl dicarbonate (24 g) in dioxane (130 cc) are added successively to a suspension of D,L-α-amino-(1,3-dithiin-5-yl)-acetic acid (19.1 g) in a mixture of dioxane (130 cc) and water (130 cc). This suspension is stirred for 18 hours at 20° C. The solvents are evaporated off under reduced pressure (20 mm Hg) at 40° C. Water (200 cc) and a saturated aqueous solution of sodium bicarbonate (50 cc) are added. The mixture is washed with ethyl acetate (3×300 cc). The aqueous phase is acidified to pH=1.5 with 4 N hydrochloric acid. Extraction is carried out with ethyl acetate (2×250 cc). The combined organic extracts are washed with a saturated solution of sodium chloride (150 cc) and dried over sodium sulphate. The solution is treated with decolorising charcoal and then filtered and concentrated to dryness under reduced pressure (20 mm Hg) at 30° C. D,L-α-Tert.-butoxycarbonylamino-(1,3-dithiin-5-yl)-acetic acid (26 g) is obtained in the form of a hard white foam.

The following Examples describe the use of the new compounds.

Preparation of
7-[α-amino-(1,3-dithiin-5-yl-acetamido]2-carboxy-3-methyl-8-oxo-5-thia-1-azabicyclo[4.2.0]-oct-2-ene

EXAMPLE A

Triethylamine (6.25 cc) is added, whilst stirring, to a solution of D,L-α-tert.-butoxycarbonylamino-(1,3-dithiin-5-yl)-acetic acid (13 g) in tetrahydrofurane (160 cc). The solution is cooled to −10° C. and isobutyl chloroformate (5.8 cc) is added dropwise. The reaction mixture is stirred for 10 minutes at −10° C. and a solution of 7-amino-2-carboxy-3-methyl-8-oxo-5-thia-1-azabicyclo[4.2.0]oct-2-ene (9.54 g) in a mixture of tetrahydrofurane (140 cc), water (140 cc) and triethylamine (6.25 cc) is then added. The reaction mixture is stirred at 0° C. for 30 minutes and then at 20° C. for 90 minutes. The solvents are evaporated off under reduced pressure (20 mm Hg) at 30° C. Water (300 cc) and a saturated aqueous solution of sodium bicarbonate (50 cc) are added and extraction is then carried out with ethyl acetate (500 cc). the aqueous phase is separated off and acidified to pH=2.0 by adding 4 N hydrochloric acid in the presence of ethyl acetate (500 cc). The organic phase is separated off and the aqueous layer is re-extracted with ethyl acetate (200 cc). The last two organic phases are combined and washed with a saturated aqueous solution of sodium chloride (150 cc) and then dried over sodium sulphate and filtered in the presence of decolorising charcoal. The filtrate is concentrated to dryness under reduced pressure (20 mm Hg) at 30° C. to obtain 7-[D,L-α-tert. butoxycarbonylamino-(1,3-dithiin-5-yl)-acetamido]-2-carboxy-3-methyl-8-oxo-5-thia-1-azabicyclo[4.2.0]oct-2-ene (18.7 g) in the form of a hard white foam.

7-[D,L-α-Tert.-butoxycarbonylamino-(1,3-dithiin-5-yl)-acetamido]-2-carboxy-3-methyl-8-oxo-5-thia-1-azabicyclo-[4.2.0]oct-2-ene (2.7 g) is dissolved in anisole (3 cc) and trifluoroacetic acid (15 cc). The solution obtained is stirred for 15 minutes at 20° C. It is concentrated to dryness under reduced pressure (0.5 mm Hg) at 30° C. The residue is taken up with ethyl acetate (15 cc), and isopropyl ether (100 cc) is then added. A white precipitate appears which is filtered off. Crude 7-[D,L-α-amino-(1,3-dithiin-5-yl)-acetamido]-2-carboxy-3-methyl-8-oxo-5-thia-1-azabicyclo[4.2.0]oct-2-ene trifluoroacetate (2.4 g) is thus obtained in the form of a white solid.

A solution of 7-[D,L-α-amino-(1,3-dithiin-5-yl)-acetamido]-2-carboxy-3-methyl-8-oxo-5-thia-1-azabicyclo-[4.2.0]oct-2-ene trifluoroacetate (11.9 g) in distilled water (500 cc) is extracted with ethyl acetate (3×100 cc). The aqueous phase is treated with moist Amberlite IR-45 resin ($OH^\ominus$) (50 cc) until the pH has been stabilised at approximately 5.25 (about one hour). The resin is filtered off. The aqueous phase is lyophilised. 7-[D,L-α-Amino-(1,3-dithiin-5-yl)-acetamido]-2-carboxy-3-methyl-8-oxo-5-thia-1-azabicyclo[4.2.0]oct-2-ene (5.7 g) is thus obtained and has the following characteristics: $[\alpha]_D^{20} = +131.2 \pm 2°$ (c=0.98; water).

Elementary analysis: % Calculated: C 43.39; H 4.42; N 10.84; O 16.52; S 24.83; % Found: C 42.6; H 3.8; N 10.7; S 24.6.

IR spectrum: characteristic bands
   3,300-2,200 $cm^{-1}$ (NH of amide and $NH_3^+$)
   1,755 $cm^{-1}$: carbonyl of β-lactam
   1,685 $cm^{-1}$: —CONH—
   1,575 $cm^{-1}$: —COOH

EXAMPLE B

Triethylamine (49 cc) is added to a solution of D-α-tert.-butoxycarbonylamino-(1,3-dithiin-5-yl)-acetic acid (102 g) in tetrahydrofurane (1,330 cc). The mixture is cooled to −10° C. and isobutyl chloroformate (48.4 cc) is added dropwise. The reaction mixture is stirred for 15 minutes at −10° C. and a solution of 7-amino-2-carboxy-3-methyl-8-oxo-5-thia-1-azabicyclo[4.2.0]oct-2-ene (75 g) in a mixture of tetrahydrofurane (1,190 cc) and triethylamine (49 cc) is then added. The reaction mixture is stirred at 0° C. for 1 hour and then at 20° C. for 2 hours. The solvent is evaporated off under reduced pressure (20 mm Hg) at 40° C. Water (1,000 cc) and a saturated aqueous solution of sodium bicarbonate (200 cc) are added and extraction is then carried out with ethyl acetate (1,000 cc). The aqueous phase is acidified to pH=2 by adding 4 N hydrochloric acid in the presence of ethyl acetate (1,000 cc). The organic phase is separated off and a further extraction is carried out with ethyl acetate (2×500 cc). The organic phases are combined, washed with a saturated aqueous solution of sodium chloride (1,000 cc), dried over magnesium sulphate, filtered and concentrated to dryness under reduced pressure (20 mm Hg) at 30° C. The residue is treated with cyclohexane (1,500 cc). The insoluble material is filtered off and dried. Crude 7-[D-α-tert.-butoxycarbonylamino-(1,3-dithiin-5-yl)-acetamido]-2-carboxy-3-methyl-8-oxo-5-thia-1-azabicyclo[4.2.0]oct-2-ene (158.5 g) is thus obtained in the form of a white powder.

The product (354.5 g) obtained under the conditions described above is dissolved in methanol (1,770 cc) at 35° C. Dicyclohexylamine (145 cc) and then acetone (1,770 cc) are added. The mixture is allowed to stand for 90 minutes at 0° C. and the crystals are then filtered off and dried under reduced pressure (1 mm Hg). The dicyclohexylamine salt of 7-[D-α-tert.-butoxycarbonylamino-(1,3-dithiin-5-yl)-acetamido]-2-carboxy-3-methyl-8-oxo-5-thia-1-azabicyclo[4.2.0]oct-2-ene (326.4 g) is thus obtained in the form of white crystals.

A suspension in water (300 cc) of the salt (29.5 g) thus obtained is acidified to pH=2 by adding 4 N hydrochloric acid in the presence of ethyl acetate (300 cc). The organic phase is separated off and a further two extractions are carried out with ethyl acetate (150 cc in total). The organic phases are combined, washed with a saturated aqueous solution of sodium chloride (150 cc), dried over sodium sulphate, filtered and concentrated to dryness under reduced pressure (20 mm Hg) at 30° C. 7-[D-α-Tert.-butoxycarbonylamino-(1,3-dithiin-5-yl)-acetamido]-2-carboxy-3-methyl-8-oxo-5-thia-1-azabicyclo[4.2.0]oct-2-ene (21.5 g) is thus obtained in the form of a white solid.

IR spectrum (KBr): characteristic bands
   3,320 $cm^{-1}$ (NH of amide and carbamate)
   1,770 $cm^{-1}$ (carbonyl of the β-lactam)
   1,700 $cm^{-1}$ (carbonyl of the acid and carbamate)
   1,680 $cm^{-1}$ (carbonyl of the amide)
   1,390 and 1,365 $cm^{-1}$ (tert.-butyl)

A solution of 7-[D-α-tert.-butoxycarbonylamino(1,3-dithiin-5-yl)-acetamido]-2-carboxy-3-methyl-8-oxo-5-thia-1-azabicyclo[4.2.0]oct-2-ene (20.3 g) in trifluoroacetic acid (200 cc) is stirred for 20 minutes at about 20° C. This solution is added, in the course of 30 minutes and whilst stirring, to ethyl ether (1,000 cc.) at 0° C. The precipitate is filtered off and dried under reduced pressure (1 mm Hg) at 20° C. 7-[D-α-Amino-(1,3-dithiin-5-yl)-acetamido]-2-carboxy-3-methyl-8-oxo-5-thia-1-azabicyclo-[4.2.0]oct-2-ene trifluoroacetate (15.7 g) is thus obtained and is dissolved in acetone (750 cc). Triethylamine (3.2 cc) is then added in order to obtain a pH of 4.8. The precipitate is filtered off and washed with ethyl ether (400 cc). 7-[D-α-Amino-(1,3-dithiin-5-yl)-acetamido]-2-carboxy-3-methyl-8-oxo-5-thia-1-azabicyclo[4.2.0]oct-2-ene (10.6 g) is thus obtained in the form of a beige solid.

The 7-[D-α-amino-(1,3-dithiin-5-yl)-acetamido]-2-carboxy-3-methyl-8-oxo-5-thia-1-azabicyclo[4.2.0]oct-2-ene (14.45 g) prepared in this way is dissolved in water (750 cc) and acetonitrile (750 cc) is then added. After one hour, the crystals are filtered off and dried under reduced pressure (1 mm Hg) at 20° C. 7-[D-α-Amino-(1,3-dithiin-5-yl)-acetamido]-2-carboxy-3-methyl-8-oxo-5-thia-1-azabicyclo[4.2.0]oct-2-ene (9.8 g) is thus obtained in the form of white crystals.

$[\alpha]_D^{20} = +137 \pm 2°$ (c=1, 0.1 N sodium carbonate).

Elementary analysis: % Calculated: C 43.39; H 4.42; N 10.84; O 16.52; S 24.83. % Found: C 43.9; H 4.9; N 10.3; O 16.0; S 23.5.

EXAMPLE C

7-Amino-3-methyl-8-oxo-2-pivaloyloxymethoxycarbonyl-5-thia-1-azabicyclo[4.2.0]oct-2-ene (11.3 g) and dicyclohexylcarbodiimide (7.1 g) are added to a solution of D-α-tert.-butoxycarbonylamino-(1,3-dithiin-5-yl)-acetic acid (10 g) in dimethylformamide (100 cc). The reaction mixture is stirred for 2 hours and then filtered. The filtrate is diluted with ethyl acetate (300 cc) and water (500 cc). The organic phase is decanted and washed with water (100 cc) and then with a saturated aqueous solution of sodium bicarbonate (100 cc) and is then dried over sodium sulphate and filtered in the presence of decolorising characoal. The filtrate is concentrated to dryness under reduced pressure (20 mm Hg) at 30° C. The residue is chromatographed on a column (diameter 3.5 cm, height 35 cm) containing silica (150 g). Elution is carried out successively with mixtures of ethyl acetate and cyclohexane of increasing ethyl acetate concentration (10/90 by volume, 500 cc; 20/80 by volume, 500 cc; 30/70 by volume, 500 cc; 40/60 by volume, 2,000 cc). 200 cc fractions are collected Fractions 14 to 21 are concentrated to dryness under reduced pressure (20 mm Hg) at 30° C. 7-[D-α-Tert.-butoxycarbonylamino-(1,3-dithiin-5-yl)-acetamido]-3-methyl-8-oxo-2-pivaloyloxymethoxycarbonyl-5-thia-1-azabicyclo[4.2.0]oct-2-ene (8 g) is thus obtained in the form of a hard orange foam.

The product thus prepared is dissolved in trifluoroacetic acid (50 cc) and stirred for 15 minutes at 20° C. The mixture is concentrated to dryness under reduced pressure (0.5 mm Hg) at 30° C. The residue is dissolved in water (200 cc). The solution is washed with ether (100 cc). The aqueous phase is covered with ethyl acetate (250 cc) and stirred. A saturated aqueous solution of sodium bicarbonate (100 cc) is added, whilst stirring. The organic phase is decanted, dried over sodium sulphate and filtered in the presence of decolorising charcoal. The filtrate is concentrated to 15 cc under reduced pressure (20 mm Hg) at 30° C. Ethyl ether (100 cc) is added and a 2.7 N solution of anhydrous hydrochloric acid in ether (10 cc) is then added dropwise. The mixture is stirred for 10 minutes and the precipitate is then filtered off. 7-[D-α-Amino-(1,3-dithiin-5-yl)-acetamido]-3-methyl-2-pivaloyloxymethoxycarbonyl-8-oxo-5-thia-1-azabicyclo[4.2.0]oct-2-ene hydrochloride (4.8 g) is thus obtained in the form of a white powder.

Elementary analysis: % Calculated: C 44.64; H 5.24; Cl 6.59; N 7.81; O 17.84; S 17.88. % Found: C 45.3; H 5.4; Cl 6.7; N 7.9; S 17.7.

We claim:

1. The 1,3-dithiinoacetic acid of the formula:

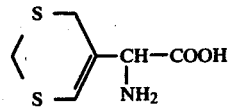

in which the amine function is free or protected by a tert.-butoxycarbonyl or 2,2,2-trichloroethoxycarbonyl radical, in its D, L and D,L forms.

2. A compound as claimed in claim 1 which is an α-amino-(1,3-dithiin-5-yl)-acetic acid in the D-, L-, or D,L-form.

3. A process for the preparation of an acid according to claim 1, which comprises saponifying an ester of the general formula:

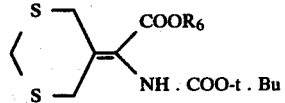

in which $R_6$ represents an alkyl radical containing 1 to 4 carbon atoms, and then optionally separating the optically active forms of the acid obtained, and optionally removing the protective tert.-butoxycarbonyl group of the amine function.

4. α-Formylamino-(1,3-dithiin-5-yl)-acetic acid.

5. The ester of the formula:

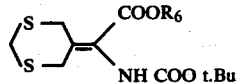

in which $R_6$ represents an alkyl radical containing 1 to 4 carbon atoms.

* * * * *